(12) United States Patent
Weidner et al.

(10) Patent No.: US 9,057,136 B2
(45) Date of Patent: Jun. 16, 2015

(54) PRODUCTION OF LOW TEMPERATURE ELECTROLYTIC HYDROGEN

(75) Inventors: John W. Weidner, Columbia, SC (US); Charles E. Holland, Cayce, SC (US)

(73) Assignee: University of South Carolina, Columbia, SC (US)

(*) Notice: Subject to any disclaimer, the term of this patent is extended or adjusted under 35 U.S.C. 154(b) by 1173 days.

(21) Appl. No.: 11/911,116

(22) PCT Filed: Apr. 12, 2006

(86) PCT No.: PCT/US2006/013558
§ 371 (c)(1),
(2), (4) Date: Jul. 18, 2008

(87) PCT Pub. No.: WO2006/110780
PCT Pub. Date: Oct. 19, 2006

(65) Prior Publication Data
US 2009/0000956 A1  Jan. 1, 2009

Related U.S. Application Data

(60) Provisional application No. 60/670,393, filed on Apr. 12, 2005.

(51) Int. Cl.
*C25B 1/02* (2006.01)
*C25B 1/22* (2006.01)
*C25B 1/00* (2006.01)

(52) U.S. Cl.
CPC .... *C25B 1/02* (2013.01); *C25B 1/22* (2013.01)

(58) Field of Classification Search
CPC ................................................ C25D 1/02–1/12
USPC .................................................. 205/628–639
See application file for complete search history.

(56) References Cited

U.S. PATENT DOCUMENTS

| | | | |
|---|---|---|---|
| 4,059,496 A | 11/1977 | Schulten et al. | |
| 4,192,726 A | 3/1980 | Pangborn et al. | |
| 4,244,794 A * | 1/1981 | Hollabaugh et al. | ........... 205/554 |
| 4,314,984 A * | 2/1982 | Lawson et al. | ................ 423/579 |
| 4,332,650 A | 6/1982 | Foh et al. | |
| 4,412,895 A | 11/1983 | Lu | |
| 4,414,092 A * | 11/1983 | Lu et al. | ........................ 204/294 |
| 5,458,744 A * | 10/1995 | Robinson et al. | ............. 205/554 |
| 5,824,199 A | 10/1998 | Simmons et al. | |

(Continued)

OTHER PUBLICATIONS

Eames, D.J.; Newman, J. Electrochemical Conversion of Anhydrous HCl to Cl2 Using a Solid-Polymer-Electrolyte Electrolysis Cell, Journal of the Electrochemical Society, 1995, 3619-3625.*

(Continued)

*Primary Examiner* — Nicholas A Smith
*Assistant Examiner* — Brian W Cohen
(74) *Attorney, Agent, or Firm* — Dority & Manning, P.A.

(57) ABSTRACT

In one embodiment of the present disclosure, a process for electrochemical hydrogen production is provided. The process includes providing an electrochemical cell with an anode side including an anode, a cathode side including a cathode, and a membrane separating the anode side from the cathode side. The process further includes feeding molecules of at least one gaseous reactant to the anode, oxidizing one or more molecules of the gaseous reactant at the anode to produce a gas product and protons, passing the protons through the membrane to the cathode, and reducing the protons at the cathode to form hydrogen gas.

4 Claims, 7 Drawing Sheets

(56) References Cited

U.S. PATENT DOCUMENTS

| | | | |
|---|---|---|---|
| 5,855,748 | A | 1/1999 | Law, Jr. et al. |
| 5,855,759 | A | 1/1999 | Keating et al. |
| 5,863,395 | A | 1/1999 | Mah et al. |
| 5,868,912 | A | 2/1999 | Reichert et al. |
| 5,891,318 | A | 4/1999 | Freire et al. |
| 5,891,319 | A | 4/1999 | Freire et al. |
| 5,961,795 | A | 10/1999 | Mah et al. |
| 5,976,346 | A | 11/1999 | Freire et al. |
| 6,001,226 | A | 12/1999 | Freire et al. |
| 6,010,612 | A | 1/2000 | Freire et al. |
| RE37,042 | E | 2/2001 | Trainham, III et al. |
| 6,203,675 | B1 | 3/2001 | Zimmerman et al. |
| 7,261,874 | B2 * | 8/2007 | Lahoda et al. ............. 423/648.1 |
| 2002/0070124 | A1 | 6/2002 | Andrews et al. |
| 2005/0077187 | A1 * | 4/2005 | Nakagiri ...................... 205/637 |

OTHER PUBLICATIONS

Sivasubramanian et al., "Electrochemical Hydrogen Production from Thermochemical Cycles Using a Proton Exchange Membrane Electrolyzer", as submitted for publication in the International Journal of Hydrogen Energy, vol. 32, Issue 4, Mar. 2007, pp. 463-468.

Lu et al., "Recent Developments in the Technology of Sulphur Dioxide Depolarized Electrolysis", Journal of Applied Electrochemistry, vol. 11, 1981, pp. 347-355.

Motupally et al. "Recycling Chlorine from Hydrogen Chloride: A New and Economical Electrolytic Process", The Electrochemical Society Interface, Fall 1998, pp. 32-36.

International Search Report, mailed Jun. 19, 2008—3 pages.

* cited by examiner

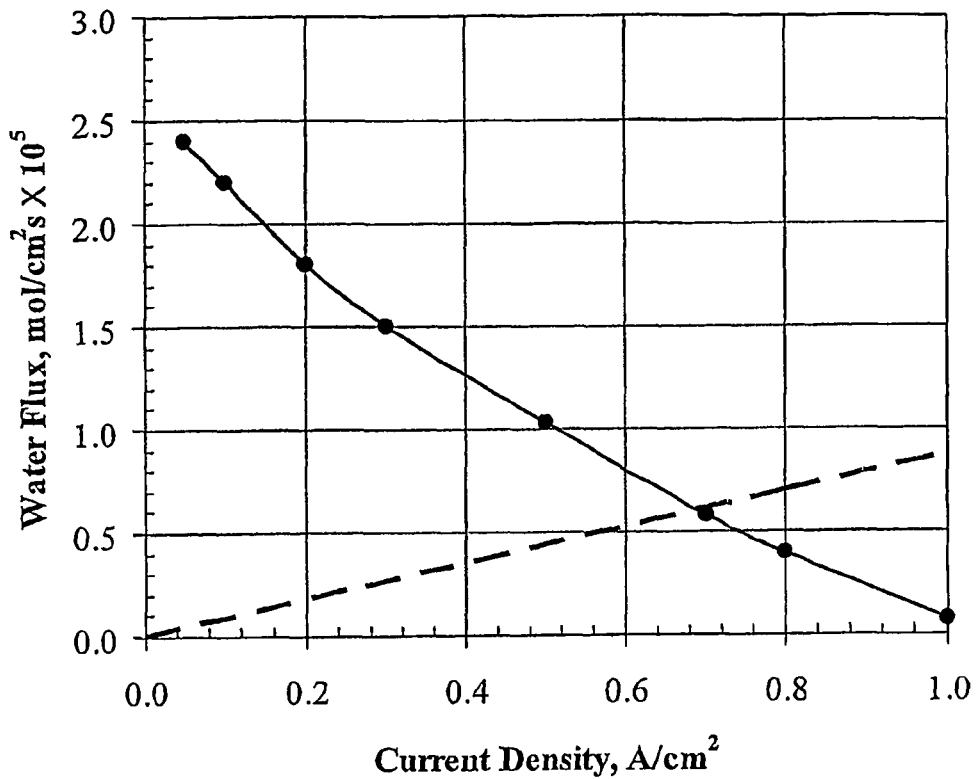
Figure 5: Flux of water across a 115 Nafion membrane as a function of current density (T = 80°C). The symbols are the data obtained experimentally for the HCl electrolyzer. The dashed line is the stoichiometric amount of water required in Reaction [1] (oxidation of $SO_2$ to $H_2SO_4$).

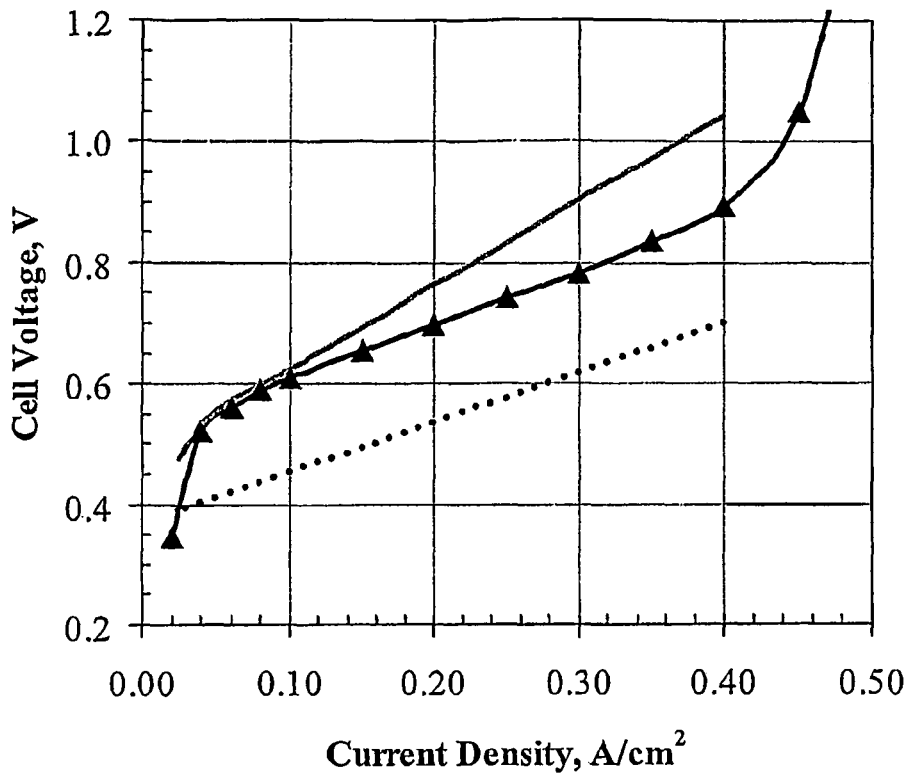

Figure 6: The current-voltage response for $SO_2$ electrolysis. The black triangles (▲) are from the PEM electrolyzer at 80°C and 1.0 atm with a platinum loading on the anode and cathode of 0.66 and 0.7 mg/cm² respectively. The solid gray line are data from Lu *et al.* [6] in an aqueous phase electrolyzer at 50°C and 1 atm, with a platinum loading on the anode and cathode loading of 7 mg/cm² and 10 mg/cm², respectively. The dotted line is the targeted cell performance in prior art experiments at 100°C and 5-20 atm, which was not achieved.

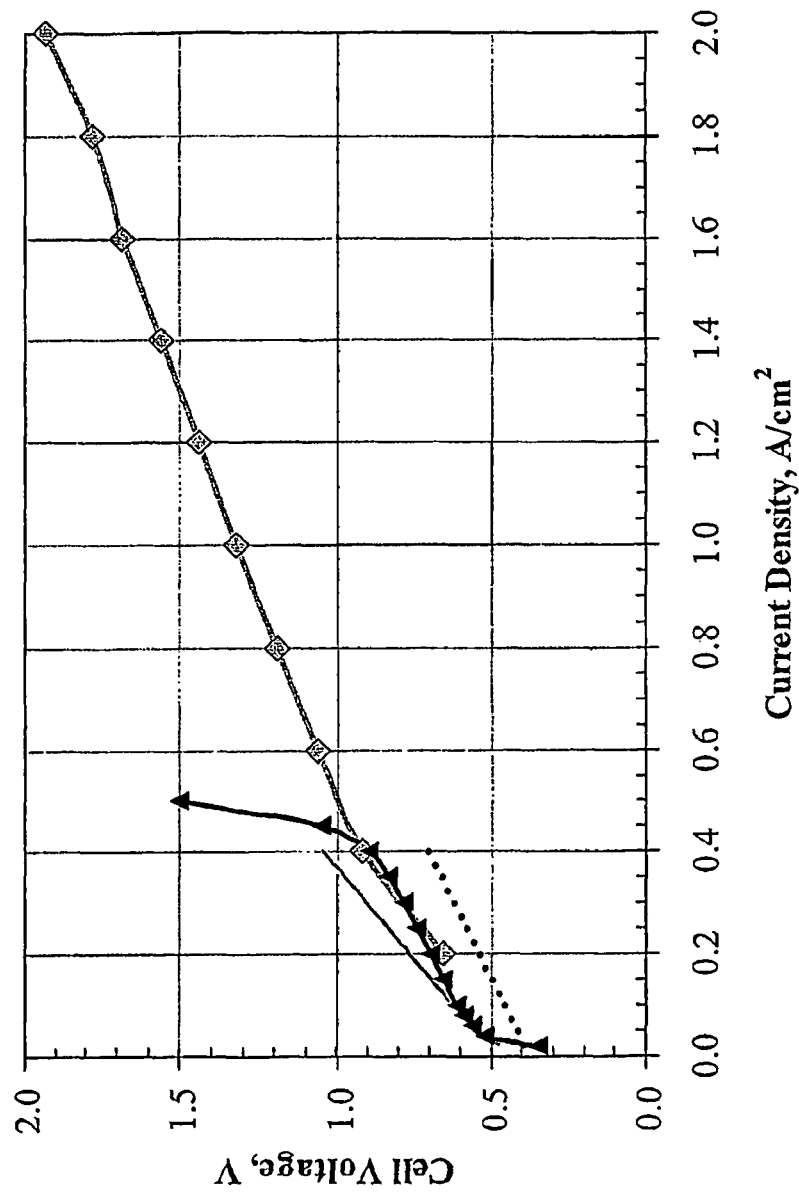
Figure 7: The current-voltage response for $SO_2$ (▲) and HBr (◆) electrolysis in a PEM electrolyzer. The results for the $SO_2$ electrolysis are the same as that given in Figure 5 but with a wider voltage scale. The HBr electrolyzer was operated at 80°C, 1.0 atm, and 50% conversion with a $RuO_2$ loading on the anode and cathode of 2.0 mg/cm².

PRODUCTION OF LOW TEMPERATURE ELECTROLYTIC HYDROGEN

CROSS REFERENCE TO RELATED APPLICATION

The present application claims benefit of United States Provisional Application Ser. No. 60/670,393 having a filing date of Apr. 12, 2005 and PCT Application No. PCT/US2006/013558 filed on Apr. 12, 2006, both of which are incorporated by reference.

BACKGROUND

Recent advances in fuel cell technology and an increasing demand for hydrogen are driving the need for the development of more efficient methods to produce hydrogen. Methods for efficient hydrogen production include utilization of thermochemical cycles. Thermochemical cycles produce hydrogen through a series of chemical reactions that result in the splitting of water at much lower temperatures than direct thermal dissociation. The chemical species in such reactions are recycled resulting in the consumption of only heat and water to produce hydrogen and oxygen. Since water rather than hydrocarbons are used as the source of hydrogen, there are no carbon dioxide emissions and the hydrogen produced is highly pure.

There are many known thermochemical cycles which can produce hydrogen from water. However, only a select few thermochemical cycles are suitable for large-scale applications and even these present difficulties. Certain problems with utilizing such thermochemical cycles have been resolved electrochemically through the use of aqueous-phase anode streams. However, aqueous-phase electrolysis suffers from low current densities and difficult product separation. Improved performance of electrolytic cells is desirable to improve the efficiency of promising thermochemical cycles. Thus, a need exists for a system which can improve the electrochemical step in thermochemical cycles.

SUMMARY

The present disclosure recognizes and addresses the foregoing needs as well as others. In one embodiment of the present disclosure, a process for electrochemical hydrogen production is provided. The process includes providing an electrochemical cell with an anode side including an anode, a cathode side including a cathode, and a membrane separating the anode side from the cathode side. The process further includes feeding molecules of at least one gaseous reactant to the anode, oxidizing one or more molecules of the gaseous reactant at the anode to produce a gas product and protons, passing the protons through the membrane to the cathode, and reducing the protons at the cathode to form hydrogen gas.

In certain embodiments, the gaseous reactant may be selected from HCl, $SO_2$, and HBr. In certain embodiments, the process may include feeding molecules of $H_2O$ to the cathode side and passing one or more $H_2O$ molecules through the membrane to the anode side. In certain embodiments, the membrane may be a polymer exchange membrane. In some embodiments, the electrochemical cell may be operated at a pressure of about 1 atm to about 20 atm. In some embodiments, the electrochemical cell may be operated at a temperature of about 50° C. to about 120° C. In some embodiments, the membrane may be coated with a catalyst.

In another embodiment of the present disclosure, a process for electrochemical hydrogen production is provided. The process includes providing an electrochemical cell with an anode side including an anode, a cathode side including a cathode, and a membrane separating the anode side from the cathode side. The process further includes feeding molecules of gaseous reactant selected from HCl, $SO_2$, and HBr to the anode, feeding molecules of $H_2O$ to the cathode side, oxidizing one or more molecules of the gaseous reactant at the anode to produce a gas product and protons, recycling one or more molecules of gaseous reactant from the electrochemical cell unreacted to the anode, passing the protons through the membrane to the cathode, passing one or more $H_2O$ molecules through the membrane to the anode side, and reducing the protons at the cathode to form hydrogen gas.

In still another embodiment of the present disclosure, a process for electrochemical hydrogen production is provided. The process includes providing an electrochemical cell with an anode side including an anode, a cathode side including a cathode, and a membrane separating the anode side from the cathode side. The process further includes feeding molecules of gaseous $SO_2$ to the anode, feeding molecules of $H_2O$ to the cathode side, passing one or more $H_2O$ molecules through the membrane to the anode side, oxidizing one or more molecules of the gaseous $SO_2$ and combining with the $H_2O$ at the anode to produce $H_2SO_4$ and hydrogen protons, passing the protons through the membrane to the cathode, and reducing the protons at the cathode to form hydrogen gas.

DESCRIPTION OF THE DRAWINGS

A full and enabling disclosure, including the best mode thereof to one of ordinary skill in the art, is set forth more particularly in the remainder of the specification, including reference to the accompanying figures in which:

FIG. 5 is a graph illustrating flux of water as a function of current density;

FIG. 6 is a graph illustrating cell voltage as a function of current density;

FIG. 7 is a graph illustrating cell voltage as a function of current density.

DETAILED DESCRIPTION

Reference will now be made in detail to the embodiments of the disclosure, examples of which are illustrated in the accompanying drawings. While the disclosure will be described in conjunction with the preferred embodiments, it will be understood that they are not intended to limit the disclosure to these embodiments. On the contrary, the disclosure is intended to cover alternatives, modifications and equivalents, which can be included within the spirit and scope of the disclosure as defined by the appended claims. Furthermore, in the following detailed description of the present disclosure, numerous specific details are set forth in order to provide a thorough understanding of the present disclosure. However, it will be obvious to one of ordinary skill in the art that the present disclosure can be practiced without these specific details. In other instances, well-known methods, procedures, and components have not been described in detail as not to unnecessarily obscure aspects of the present disclosure.

In general, the present disclosure is directed to production of low temperature electrolytic hydrogen. The present disclosure provides an economical route for production of pure hydrogen by disclosing an improved electrolysis process for thermochemical cycles which involves low temperature production of hydrogen.

Thermochemical cycles can produce hydrogen through a series of chemical reactions where the net result is the production of hydrogen and oxygen from water at much lower temperatures than direct thermal decomposition. Although numerous thermochemical cycles have been identified, many are unworkable due to low efficiency or excessive temperature requirements.

For example, certain sulfur-based processes all have the common oxygen generating, high-temperature step, which is the decomposition of sulfuric acid to sulfur dioxide and oxygen at temperatures in the 850-1000° C. range. In the sulfur-iodine cycle, the $SO_2$ is converted back to $H_2SO_4$ and hydrogen is produced via a two-step process involving iodine. The distillation of HI from solution and concurrent decomposition to iodine is the most difficult process issue for the iodine containing portion of the cycle.

However, as described in P. W. Lu, E. R. Garcia, and R. L. Ammon, *J. Appl. Electrochem.*, 11, 347 (1981), a hybrid process exists in which $SO_2$ is electrochemically oxidized to $H_2SO_4$ from a liquid-phase anode stream. The hybrid sulfer process is:

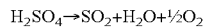
$H_2SO_4 \rightarrow SO_2 + H_2O + \frac{1}{2}O_2$

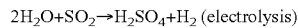
$2H_2O + SO_2 \rightarrow H_2SO_4 + H_2$ (electrolysis)

Figure 1:
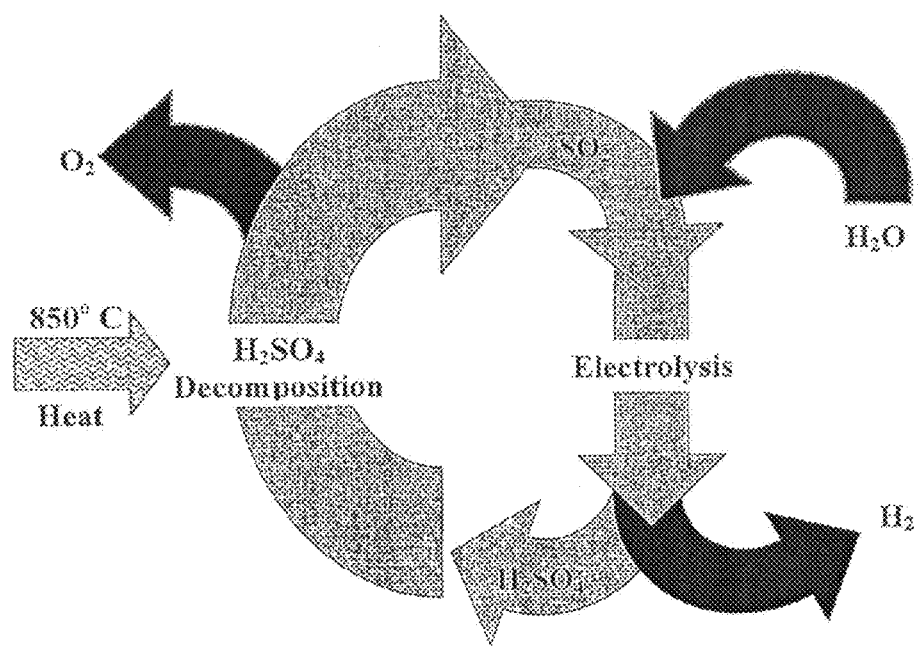
FIG. 1 depicts hybrid sulfur thermochemical cycle.

A diagram of the hybrid-sulfur process is Illustrated as FIG. 1. However, improved performance of the electrolytic cell is needed to improve the overall efficiency of this promising cycle.

Figure 2:
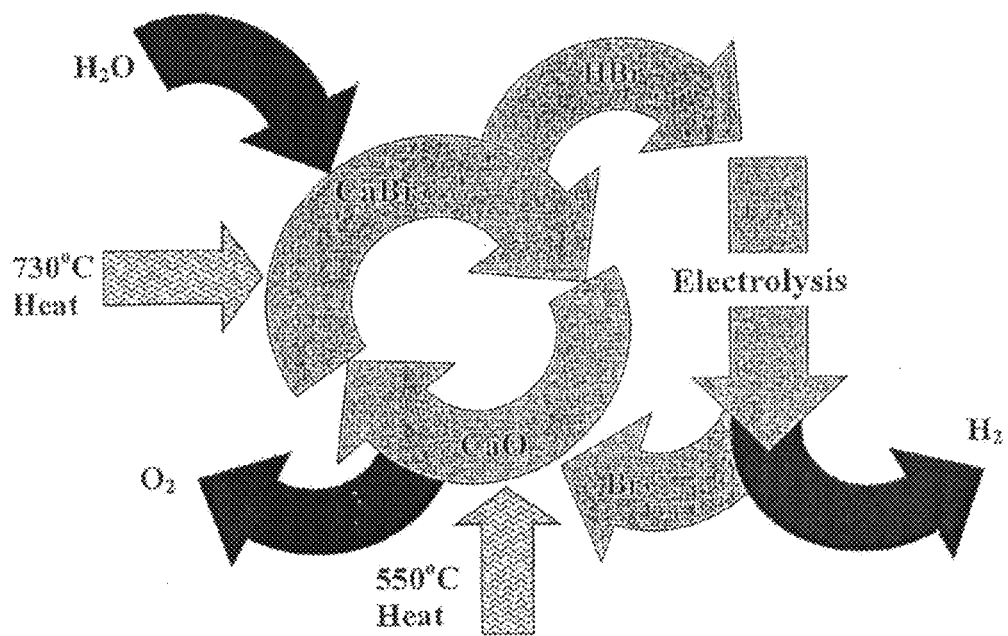
FIG. 2 depicts a modified calcium-bromide thermochemical cycle.

In addition, calcium-bromide-based cycles also have the potential of high efficiencies but with lower temperature requirements (~750° C.) than the sulfur-based cycles. The common step in these cycles is the conversion of CaO and $Br_2$ to $CaBr_2$ and $O_2$ at approximately 550° C., and the conversion of $CaBr_2$ back to CaO and HBr at 730° C. The second recycle step, converting HBr to $Br_2$ and generating hydrogen, can be done thermally in a solid-gas, fixed bed reactor of iron oxide, which in turn needs to be regenerated. The iron reaction beds can be eliminated in a modified Ca—Br cycle by converting HBr directly to $Br_2$ and $H_2$ in a single step (see also, illustration in FIG. 2):

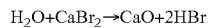
$H_2O + CaBr_2 \rightarrow CaO + 2HBr$

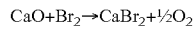
$CaO + Br_2 \rightarrow CaBr_2 + \frac{1}{2}O_2$

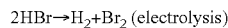
$2HBr \rightarrow H_2 + Br_2$ (electrolysis)

This direct conversion can be performed electrochemically or in a plasma process. However, aqueous-phase electrolysis of HBr suffers from low current densities due to liquid-phase mass-transfer limitations and difficult product separation due to dissolution of $Br_2$ in solution.

Thus, in one aspect of the present disclosure, anode reactions are carded out in the gas phase of a proton exchange membrane electrolyzer to improve the electrochemical step in certain thermochemical cycles.

In accordance with the one embodiment of the present disclosure, there is provided an electrochemical cell for the direct production of hydrogen gas from one or more gaseous reactants. This cell will be described with respect to one embodiment of the present disclosure, which directly produces hydrogen gas from $SO_2$ and $H_2O$. However, such a cell may alternatively be used to produce hydrogen gas from other reactants including HCl and HBr. Such a cell is shown generally at 10 in FIG. 3. In this embodiment, $H_2SO_4$ gas, as well as hydrogen, is produced by this cell.

Figure 3:
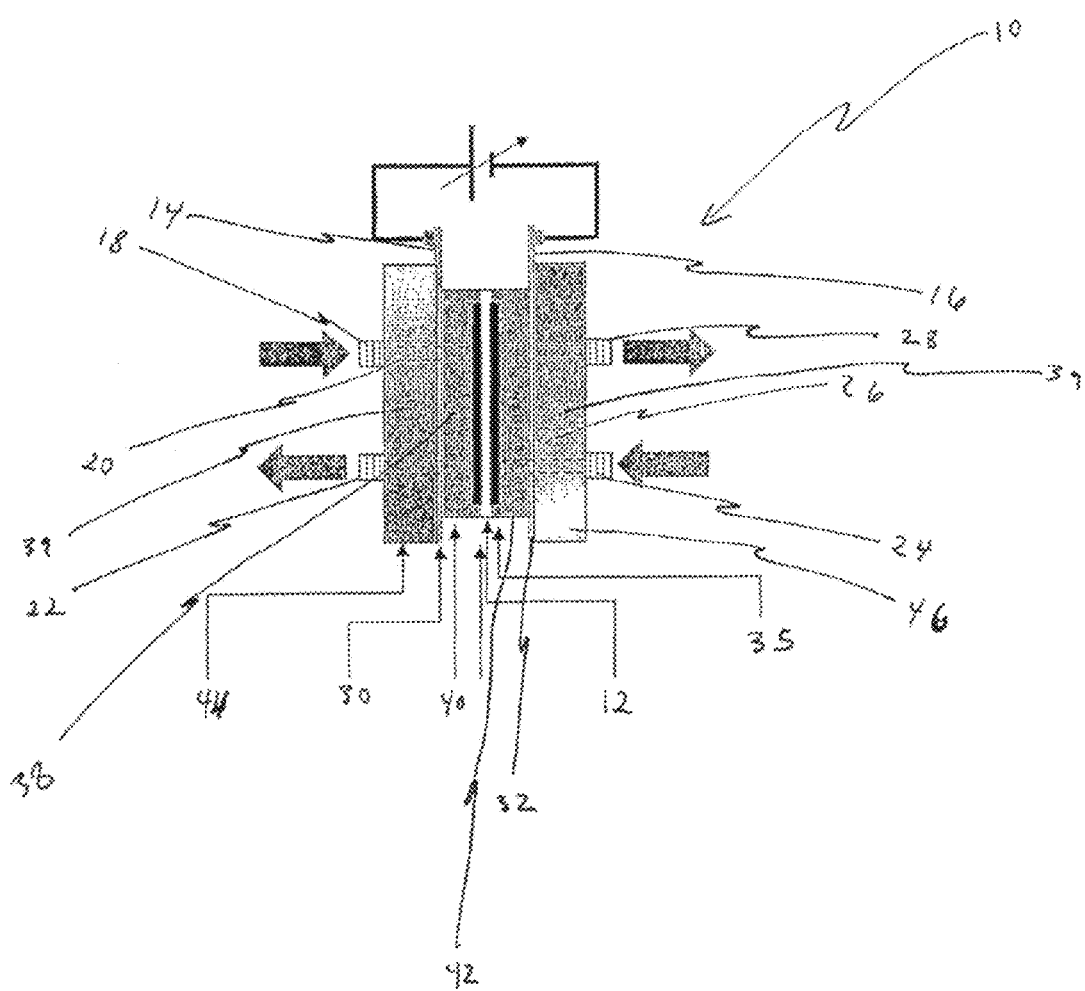
FIG. 3 depicts a schematic diagram of an electrochemical cell in accordance with one aspect of the present disclosure.

The electrochemical cell 10 comprises a cation-transporting membrane 12 as depicted in FIG. 3. More specifically, membrane 12 may be a proton-conducting membrane. Membrane 12 can be a commercial cationic membrane made of one or more fluoro and/or perfluoropolymers. Suitable cationic membranes, which are made of hydrated, copolymers of polytetrafluoroethylene and poly-sulfonyl fluoride vinyl ether-containing pendant sulfonic acid groups, are offered by E.I. du Pont de Nemours and Company of Wilmington, Del. under the trademark "NAFION" (hereinafter referred to as NAFION). In particular, a poly[perfluorosulfonic] acid membrane (NAFION® 115) can be utilized.

Electrochemical cell 10 also comprises a pair of electrodes, specifically, an anode 14 and a cathode 16, each disposed in contact with a respective side of the membrane as depicted in FIG. 3. Anode 14 has an anode inlet 18 which leads to an anode chamber 20, which in turn leads to an anode outlet 22. Cathode 16 has a cathode inlet 24 which leads to a cathode chamber 26, which in turn leads to a cathode outlet 28. As would be known to one skilled in the art, if electrodes are placed on opposite faces of a membrane, cationic charges are transported through the membrane from anode to cathode, while each electrode carries out a half-cell reaction.

In one embodiment of the present disclosure, molecules of gaseous $SO_2$ are transported to the surface of the anode through inlet 18. The molecules of $SO_2$ are oxidized in the gas phase and combined with $H_2O$ to produce $H_2SO_4$ and protons. The $H_2SO_4$ gas exits through anode outlet 22 as depicted in FIG. 3. The protons are transported through the membrane and reduced at the cathode as is described in more detail below.

The anode and the cathode may comprise porous, gas-diffusion electrodes. Such electrodes provide the advantage of high specific surface area, as known to one skilled in the art. The anode and the cathode comprise an electrochemically active material disposed adjacent, meaning at or under, the surface of the cation-transporting membrane. A thin film of the electrochemically active material may be applied directly to the membrane. Alternatively, the electrochemically active material may be hot-pressed to the membrane as would be known to one skilled in the art. Alternatively, the electrochemically active material may be deposited into the membrane. The electrochemically active material may comprise any type of catalytic or metallic material or metallic oxide, as long as the material can support charge transfer. Preferably, the electrochemically active material may comprise a catalyst material such as platinum, ruthenium, osmium, rhenium, rhodium, iridium, palladium, gold, titanium or zirconium and the oxides, alloys or mixtures thereof. The phrase "mixtures comprising any of these elements, oxides and alloys" means at least one of these elements, oxides and alloys mixed with at least one of any other of these elements, oxides and alloys and/or any other constituent. However, in general, the oxides of these materials are not used for the cathode. Other catalyst materials suitable for use with the present disclosure may include, but are not limited to, transition metal macrocycles in monomeric and polymeric forms and transition metal oxides, including perovskites and pyrochores.

In a hot-pressed electrode, the electrochemically active material may comprise a catalyst material on a support material. The support material may comprise particles of carbon and particles of polytetrafluoroethylene, which is sold under the trademark "TEFLON" (hereinafter referred to as TEFLON®), commercially available from E. I. du Pont de Nemours and Company of Wilmington, Del. The electrochemically active material may be bonded by virtue of the TEFLON® to a support structure 35 of carbon paper or graphite cloth and hot-pressed to the cation-transporting membrane. The hydrophobic nature of TEFLON® does not allow a film of water to form at the anode. The electrodes are preferably hot-pressed into the membrane in order to have good contact between the catalyst material and the membrane.

The loadings of electrochemically active material may vary based on the method of application to the membrane.

A current collector 30, 32, respectively, is disposed in electrical contact with the anode and the cathode, respectively, for collecting charge. In some embodiments, the current collectors are formed from copper. More specifically, the current collectors can be machined with flow channels for directing the reactant to the anode and the water added to the cathode. It is within the scope of the present disclosure that the current collectors and the flow channels may have a variety of configurations.

Figure 4:
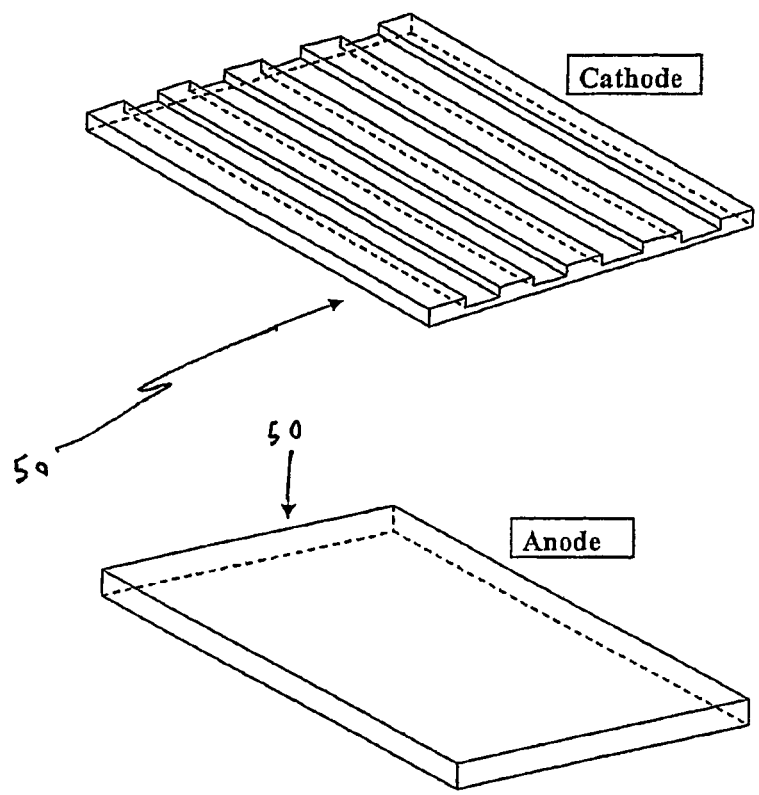
FIG. 4 depicts flow fields in accordance with one aspect of the present disclosure.

Referring to FIG. 4, flow fields 50 are depicted with the cathode channels facing away from the membrane. The channels in the cathode flow field serve to facilitate the removal of hydrogen gas bubbles and allow free flow of water. In some embodiments, the material can be SpectraCorp High Flow (HF) carbon paper with a porosity of 70%.

Referring back to FIG. 3, the current collectors may be made in any manner known to one skilled in the art. For example, the current collectors may be machined from graphite blocks impregnated with epoxy to prevent oxygen and water from leaking through the blocks. The current collectors may also be made of a porous carbon in the form of a foam, cloth or matte. The current collectors may also include thermocouples or thermistors 38 to monitor and control the temperature of the cell.

In certain embodiments, the electrochemical cell can also comprise a structural support for holding the cell together. Preferably, the support comprises a pair of backing plates 40, 42 which are torqued to high pressures to reduce the contact resistances between the current collectors and the electrodes. In addition, end plates 44, 46 may also be utilized. Such plates may be aluminum or stainless steel but are preferably a corrosion-resistant metal alloy. The plates can include heating elements 39 which are used to control the temperature of the cell. In some embodiments, cartridge heaters can be utilized. A non-conducting element, such as TEFLON® or other insulator, can be disposed between the collectors and the backing plates.

In one embodiment of the present disclosure, the electrochemical cell can also include a voltage source for supplying a voltage to the cell. The voltage source is attached to the cell through current collectors 30 and 32.

When more than one anode-cathode pair is used, such as in manufacturing, a bipolar arrangement is preferred. In the simple cell shown in FIG. 3, a single anode and cathode are shown. The current flows from the external voltage source to the cathode and returns to the external source through the lead connected to the anode. With the stacking of numerous anode-cathode pairs, it is not most convenient to supply the current in this fashion. Hence, for a bipolar arrangement, the current flows through the cell stack. This is accomplished by having the current collector for the anode and the cathode machined from one piece of material. Thus, on one face of the current collector, the gaseous reactant for the anode flows in machined channels past the anode. On the other face of the same current collector, channels are machined, and the current is used in the cathodic reaction, which produces hydrogen in this disclosure. The current flows through the repeating units of a cell stack without the necessity of removing and supplying current to each individual cell. The material selected for the current collector must be resistant to the oxidizing conditions on the anode side and the reducing conditions on the cathode side. Of course, the material must be electronically conductive. In a bipolar configuration, insulators are not interspersed in the stack as described above. Rather, there are backing plates at the ends of the stack, and these may be insulated from the adjacent current collectors.

Further in accordance with an embodiment of the present disclosure, there is provided a process for the direct production of hydrogen gas from a gaseous reactant. The gaseous reactant can comprise HCl, $SO_2$, and HBr. In certain embodiments, the production of hydrogen gas can be accomplished when the electrochemical cell is run at temperatures from about 50° C. to about 120° C. In some embodiments, the electrochemical cell temperature can range from about 60° C. to about 100° C. In still other embodiments, the electrochemical cell temperature can range from about 70° C. to about 90° C.

In some embodiments, molecules of gaseous reactant are transported to the surface of the anode through anode inlet 18 and through gas channels 34. Water is delivered to the cathode through cathode inlet 24 and through channels 36 formed in cathode current collector 32 to hydrate the membrane and thereby increase the efficiency of proton transport through the membrane. Molecules of the gaseous reactant are oxidized at the anode under the potential created by the voltage source to produce a gas product at the anode, and protons.

The gas product exits through anode outlet 22 as depicted in FIG. 3. The protons are transported through the membrane, which acts as an electrolyte. The transported protons are reduced at the cathode to produce hydrogen gas.

The hydrogen which is evolved at the interface between the electrode and the membrane exits via cathode outlet 28 as shown in FIG. 3. The hydrogen bubbles through the water.

In some embodiments, it is preferable for the membrane to be hydrated in order to have efficient proton transport. Thus, in some embodiments, the step of keeping the cathode side of the membrane moist to increase the efficiency of proton transport through the membrane may be utilized. In some embodiments, the hydration of the membrane is obtained by keeping liquid water in contact with the cathode. The liquid water passes through the gas-diffusion electrode and contacts the membrane.

In some embodiments, a water activity gradient exists across the membrane. In some embodiments, water diffuses from the cathode side to the anode side across the membrane. The flux of water across the membrane decreases with increasing current density because electro-osmotic drag pulls water from the anode to the cathode to counter the diffusion of water from the cathode to the anode. In some embodiments, the reaction rate at the anode is limited by the rate of water transport across the membrane. In such embodiments, a mass-transfer limiting current density is observed at certain current densities. In some embodiments, it is possible to extend such limiting current through utilization of thinner membranes or by humidifying the gaseous reactant prior to being fed in the electrolyzer.

As described previously, the electrochemical cell can be operated over a wide range of temperatures and pressures. Room temperature operation is an advantage, due to the ease of use of the cell. However, operation at higher temperatures provides the advantages of improved kinetics and increased electrolyte conductivity. It should be noted also that one is not restricted to operate the electrochemical cell at atmospheric pressure. In some embodiments, the electrochemical cell is operated at a pressure of about 1 atm to about 20 atm. In some embodiments, the electrochemical cell is operated at a pressure of about 1 atm to about 15 atm. In still other embodiments, the electrochemical cell is operated at a pressure of about 1 atm to about 10 atm. The cell could be run at differential pressure gradients, which change the transport characteristics of water or other components in the cell, including the membrane.

In some embodiments of the present disclosure, a portion of the gaseous reactant may be unreacted after contacting the cell and may exit the cell through the anode outlet along with the product gas. It should be noted that the described system can be used to recycle other unreacted materials. Referring to FIG. 3, the system recycles the unreacted gaseous reactant back to cell 10, which includes membrane 12, anode 14, anode chamber 20, cathode 16 and cathode chamber 26 as described above. Cell 10 also includes current collectors 30, 32 having flow channels 34, 36 formed therein. In some embodiments, the unreacted portion of the gaseous reactant is separated from product gas by a separator in a separation process which may involve distillation, adsorption, extraction, membrane separation or any number of known separation techniques. The separated, unreacted portion of gaseous reactant is recycled through a line back to anode inlet 18 of electrochemical cell 10. In some embodiments, hydrogen gas exits cell 10 through cathode outlet 28 and through a line 48. Excess water may also exit through cathode outlet 28, where it is separated from hydrogen gas and recycled to cathode inlet 24 through a line.

The following Examples are intended to be purely exemplary of the disclosure. In the Examples given below, experimental data are presented which show some of the results that have been obtained by operating the first embodiment of the present disclosure for different electrode materials, temperatures, and different modes of operation. More specifically, in these experiments, the current and the cell potential were measured for three different temperatures and for two different electrode materials.

EXAMPLES

MEA Preparation: SO$_2$ Electrolyzer

The membrane electrode assembly (MEA) was prepared by the catalyst spraying/hot-pressing method. Carbon cloth, gas diffusion layers (GDLs) (ELAT-R® from ETEK) were used on both the anode and the cathode. The ink was 40 wt % Pt on carbon and NAFION® dissolved in isopropanol. The NAFION® and carbon were in a 1:1 mass ratio. A mask with a square opening of 40 cm$^2$ was placed on the micro-porous carbon layer, and the ink was uniformly sprayed onto the GDL until a desired loading was achieved. The anode and cathode platinum loadings were 0.66 mg/cm$^2$ and 0.70 mg/cm$^2$, respectively. A poly[perfluorosulfonic] acid membrane (NAFION® 115® from DuPont) was placed between the catalyst-coated GDLs and hot-pressed at 2000 psia and 130° C. in a Carver hot press (Model # 3851-0). Prior to its use, the NAFION® 115 membrane was boiled in 1 N H$_2$SO$_4$ solution for 90 minutes and rinsed thoroughly with de-ionized water for 10 minutes.

MEA Preparation: HBr Electrolyzer

The MEAs were prepared with carbon cloth GDLs containing 2.0 mg/cm$^2$ of RuO$_2$ (ELAT-S® from ETEK) as the catalyst for both the anode and cathode. The 50 cm$^2$ cloths were taped at the edges with Teflon tape (3M Corporation, serial 5190) to give an active area of 40 cm$^2$. A poly[perfluorosulfonic] acid membrane (NAFION® 10510 from DuPont) was placed between the catalyst coated carbon cloths. No hot pressing was performed. Prior to use the NAFION® membrane was boiled in 1 wt % HCl and rinsed and stored in D.I. water. Immediately before assembly the membrane was wiped dry.

Proton Exchange Membrane Electrolyzer

The electrolyzer for both processes used two back plates that contained 80 wt % graphite and 20 wt % fluoro inert polymer composite (Diabond® F100). The back plates were followed by copper current collectors and stainless steel end plates on both sides. Flow fields made out of 3.385 mm thick carbon paper (SpectraCorp 2050-A) were place inside a 3.385 mm deep well machined into the Diabond back plates. Two Viton 'O' rings fit into grooves machined into the Diabond plates and served to seal the cell. The MEA was placed between the two flow fields, and the cell assembly was bolted together with twelve bolts by the application of a uniform torque of 60 in-lbs. A schematic of the cell assembly is depicted in FIG. 3. The only difference between the anode and cathode sides of the cell was that the latter contained carbon paper with 21 machined flow channels. Each channel was 1.4 mm deep, 1.5 mm wide and ran in the direction of flow. These channels were away from the membrane and they served to facilitate the removal of hydrogen gas bubbles and the free flow of water. A schematic of these flow fields is depicted in FIG. 4. The cell temperature was maintained at 80° C. with the aid of heating cartridges and thermocouples on the anode and cathode sides. Preheated (80° C.) de-ionized water was sent to the cathode side of the electrolyzer at a fixed rate of 130 cm$^3$/min using a FMI model QV pump. The flow of water helped to maintain the desired cell temperature and to prevent hydrogen bubbles from accumulating in the cathode. The anode feed gas was set according to the current to maintain the desired percent conversion of HBr or SO$_2$. Pressure was maintained at 1.0 atm (absolute) on both sides of the cell using back pressure regulator valves. The current to the electrolyzer was controlled using a HP model 6031A power supply.

Current-Voltage Response: SO$_2$ Electrolyzer

On the anode side of the electrolyzer, the sulfur dioxide combines with water to produce sulfuric acid via the reaction:

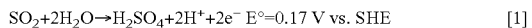
$$SO_2 + 2H_2O \rightarrow H_2SO_4 + 2H^+ + 2e^- \quad E°=0.17 \text{ V vs. SHE} \quad [1]$$

Protons pass through the membrane and recombine at the cathode to produce hydrogen via the reaction:

$$2H^+ + 2e^- \rightarrow H_2 \quad E°=0.0 \text{ V vs. SHE} \quad [2]$$

Thus the overall reaction in the electrolyzer is:

$$SO_2 + 2H_2O \rightarrow H_2SO_4 + H_2 \quad [3]$$

An experiment was performed to determine if the water needed by Reaction [1] could be provided by transport across the membrane from the cathode. This was based on the flux of water across a NAFION® 115 membrane as a function of current density. These data are plotted in FIG. 5 (symbols) along with the stoichiometric amount of water needed in Reaction [1] (dashed line). The flux of water across the membrane decreases with increasing current density because electro-osmotic drag pulls water from the anode to the cathode to counter the diffusion of water from the cathode to the anode. Although SO$_2$ in place of HCl will alter the amount of water transported across the membrane, the results in FIG. 5 suggest that no additional water needs to be fed with the SO$_2$ at current densities below 0.7 A/cm$^2$.

FIG. 6 shows the current-voltage response of the PEM electrolyzer for the oxidation of SO$_2$ to H$_2$SO$_4$ and the reduction of protons to $H_2$. Data (▲) was collected at 80° C., 1.0 atm, and 5% conversion of $SO_2$. Although this conversion is low, the voltage varied by less than 30 mV for conversions between 5-40%, which is less than the size of the symbols. The results indicated that water transported across the membrane is sufficient to sustain Reaction [1] up to current densities of 0.4 A/cm². A mass-transfer limiting current density is observed beyond this point. It is most likely that the limiting reactant in Reaction [1] is water and not $SO_2$. Therefore, it is not possible to increase the rate of Reaction [1] by increasing the voltage or the $SO_2$ flow rate. Rather, the reaction rate is limited by the rate of water transport across the membrane. The limiting current could be extended by using thinner membranes or by humidifying the $SO_2$ before it enters the electrolyzer.

FIG. 6 also shows representative data from prior art experimentation (gray line) obtained at 50° C. and 1.0 atm. The catholyte was dilute $H_2SO_4$ and the anolyte was 50 wt % $H_2SO_4$ pre-saturated with $SO_2$. The anode and cathode compartments were separated by a rubber diaphragm, and the platinum loadings were 7 mg/cm² and 10 mg/cm² on the anode and cathode, respectively. The dotted line in FIG. 6 is the targeted cell performance given by the prior art for 100° C., 5-20 atm, and 50-60 wt % sulfuric acid, which was not achieved. A cell performance of 0.5 A/cm² at 0.6 V in the Hybrid Sulfur process was estimated to provide greater overall efficiency and lower production cost than direct electrolysis of water. The data at 0.4 A/cm² shows an improvement of over 150 mV in cell voltage at 1/10th the Pt loadings.

The concentration of $H_2SO_4$ produced by the oxidation of $SO_2$ is important in determining the overall operating efficiency of the hybrid-sulfur cycle. The less water (i.e., higher $H_2SO_4$ concentration) sent to the decomposition reactor, the less energy needed to vaporize this stream. Therefore, to determine the concentration of sulfuric acid exiting the electrolyzer, the outlet liquid stream was collected at the bottom of a knock-out vessel. This solution was titrated against 1.0 N sodium hydroxide using Phenol Red as an indicator. At 0.1 and 0.4 A/cm², the reactor produced 13 and 46 wt % $H_2SO_4$, respectively. Consistent with FIG. 5, less water ends up in the sulfuric acid at higher current density since more water is consumed in the reaction and less water is transported across the membrane.

Current-Voltage Response: HBr Electrolyzer

On the anode side of the electrolyzer, the HBr is converted to $Br_2$ via the reaction:

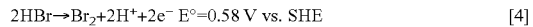
$2HBr \rightarrow Br_2 + 2H^+ + 2e^-$   E°=0.58 V vs. SHE   [4]

Protons pass through the membrane and recombine at the cathode to produce hydrogen via the reaction:

$2H^+ + 2e^- \rightarrow H_2$   E°=0.0 V vs. SHE   [5]

Thus the overall reaction in the electrolyzer is:

$2HBr \rightarrow Br_2 + H_2$   [6]

Unlike Reaction [3], no water is consumed in Reaction [6]. The purpose of adding water to the cathode side of the HBr electrolyzer is to keep the membrane wet and hence conductive, to help maintain the desired operating temperature, and the remove the hydrogen produced at the catalyst surface. FIG. 7 shows the current-voltage response of the PEM electrolyzer for the oxidation of HBr to $Br_2$ and the reduction of protons to $H_2$. The data (♦) was collected at 80° C., 1.0 atm and 50% conversion of HBr. For comparison purposes, the results from FIG. 5 are replotted on this figure. The main difference between the HBr and $SO_2$ electrolysis is that the former can be run at significantly higher current densities. This supports the conclusion that water and not $SO_2$ is the limiting reactant in Reaction [1]. Another difference between the V-I performance curves for these two reactions is the overpotentials required to carry out the reactions. For HBr electrolysis, a small activation barrier is needed to produce $Br_2$ and $H_2$, as evidenced from a cell voltage of 0.66 V at 0.2 A/cm², which is 80 mV above the equilibrium voltage of 0.58 V. In contrast, $SO_2$ electrolysis at 0.2 A/cm² requires 530 mV above the equilibrium voltage of 0.17 V. Therefore, $SO_2$ rather than HBr oxidation would benefit from improved catalyst performance. For both reactions, the linear relationship between current and voltage above 0.2 A/cm² is characteristic of the ohmic resistance of the membrane. Thinner membranes should result in a lower slope in the V-I curve. The larger current range for HBr electrolysis provides great flexibility in operating this step in the process. For example, if operating efficiency (i.e., electric power consumed for a given hydrogen production rate) is the key constraint than the cell can be run at low current densities and hence low cell voltage (i.e., high efficiency). However, if capital cost is the key constraint then the cell can be run at higher current densities, resulting in a smaller cell for given hydrogen production rate.

The results indicate electrochemical cell performance which can exceed that generally obtained in the prior art.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only and is not intended to limit the disclosure so further described in such appended claims.

What is claimed is:

1. A process for electrochemical hydrogen production by use of an electrochemical cell, said electrochemical cell including an anode side having only one inlet comprising an anode, a cathode side comprising a cathode, and a membrane separating said anode side from said cathode side, said process comprising:

feeding only molecules of gaseous $SO_2$ to said anode through the said inlet;

delivering water to said cathode, at least a portion of said water being transported across said membrane to said anode side, one or more said molecules of said $SO_2$ oxidizing at said anode to produce a gas product and protons according to the following reaction:

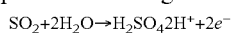
$SO_2 + 2H_2O \rightarrow H_2SO_4 2H^+ + 2e^-$ wherein no additional water is fed to the anode side such that the water transported across the membrane sustains the reaction at the anode;

said protons passing through said membrane to said cathode; and said protons being reduced at said cathode to form hydrogen gas.

2. The process of claim 1, wherein said membrane comprises a polymer exchange membrane.

3. The process of claim 1, wherein said electrochemical cell is operated at a temperature of about 80° C. throughout the process.

4. The process of claim 1, wherein the process is carried out at a pressure of about 1 atmosphere.

* * * * *

UNITED STATES PATENT AND TRADEMARK OFFICE
CERTIFICATE OF CORRECTION

PATENT NO.       : 9,057,136 B2  
APPLICATION NO.  : 11/911116  
DATED            : June 16, 2015  
INVENTOR(S)      : John W. Weidner et al.

Page 1 of 1

It is certified that error appears in the above-identified patent and that said Letters Patent is hereby corrected as shown below:

Claims

In Column 10, line 50, Claim 1: please insert a -- + -- into the formula after "$SO_2 + 2H_2O \rightarrow H_2SO_4$ ..."

Signed and Sealed this  
Fifth Day of April, 2016

Michelle K. Lee  
*Director of the United States Patent and Trademark Office*